United States Patent
Tofte Jespersen

(10) Patent No.: US 9,155,298 B2
(45) Date of Patent: Oct. 13, 2015

(54) LOADED GEL PARTICLES FOR ANTI-FOULING COMPOSITIONS

(75) Inventor: Henrik Tofte Jespersen, Kirke Hyllinge (DK)

(73) Assignee: EnCoat ApS, København (DK)

( * ) Notice: Subject to any disclaimer, the term of this patent is extended or adjusted under 35 U.S.C. 154(b) by 151 days.

(21) Appl. No.: 13/582,045

(22) PCT Filed: Mar. 2, 2011

(86) PCT No.: PCT/EP2011/053130
§ 371 (c)(1),
(2), (4) Date: Apr. 12, 2013

(87) PCT Pub. No.: WO2011/107521
PCT Pub. Date: Sep. 9, 2011

(65) Prior Publication Data
US 2013/0209389 A1    Aug. 15, 2013

(30) Foreign Application Priority Data
Mar. 2, 2010  (DK) ............................ PA 2010 70079

(51) Int. Cl.
| A61K 9/14 | (2006.01) |
| --- | --- |
| A01N 25/10 | (2006.01) |
| B01J 13/00 | (2006.01) |
| C01B 33/158 | (2006.01) |
| C09D 5/16 | (2006.01) |
| C09D 7/12 | (2006.01) |
| A61K 9/16 | (2006.01) |
| C08K 3/08 | (2006.01) |

(52) U.S. Cl.
CPC .............. *A01N 25/10* (2013.01); *B01J 13/0069* (2013.01); *C01B 33/1585* (2013.01); *C09D 5/165* (2013.01); *C09D 5/1687* (2013.01); *C09D 7/1225* (2013.01); *C09D 7/1291* (2013.01); *A61K 9/1694* (2013.01); *C08K 3/08* (2013.01)

(58) Field of Classification Search
None
See application file for complete search history.

(56) References Cited

U.S. PATENT DOCUMENTS

2005/0013843 A1  1/2005  Detty et al.
2008/0188575 A1*  8/2008  Gaspar Martinho et al. . 516/111

FOREIGN PATENT DOCUMENTS

| EP | 0364271 A2 | 4/1990 |
| --- | --- | --- |
| WO | 2007/015676 A1 | 2/2007 |
| WO | 2009/062518 A1 | 5/2009 |
| WO | 2009/062975 A1 | 5/2009 |
| WO | WO 2009062518 A1 * | 5/2009 |

OTHER PUBLICATIONS

International Search Report received for PCT Patent Application No. PCT/EP2011/053130, mailed on Feb. 7, 2012, 7 pages.

* cited by examiner

*Primary Examiner* — Susan Tran
(74) *Attorney, Agent, or Firm* — Morrison & Foerster LLP

(57) ABSTRACT

The present invention provides polishing control components for anti-fouling paints for vessels which comprise rosin or other water-degradable polymers entrapped in gel particles, such as aerogel or aeromosil particles.

14 Claims, 3 Drawing Sheets

Abietic acidPimaric acid

2 Abietic Acid

ROSIN ACID DIMER

LOADED GEL PARTICLES FOR ANTI-FOULING COMPOSITIONS

CROSS REFERENCE TO RELATED APPLICATIONS

Figure 1:
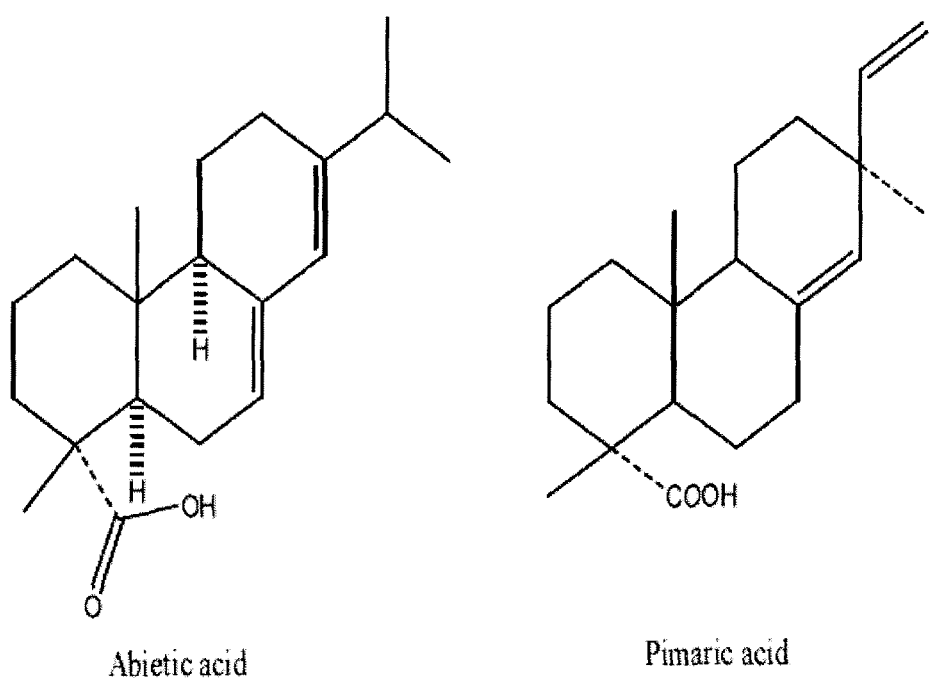

This is a U.S. National Phase patent application of PCT/EP2011/053130, filed Mar. 2, 2011, which claims priority to the Danish Patent Application No. PA 2010 70079, filed Mar. 2, 2010, each of which is hereby incorporated by reference in the present disclosure in its entirety.

FIELD OF THE INVENTION

The present invention relates to the field of polishing control components of anti-fouling compositions and paints or similar controlled leaching systems for vessels and stationary marine constructions.

BACKGROUND OF THE INVENTION

Ship surfaces exposed to seawater are inclined to settlement by animal and plant organisms. The biological process, which is termed fouling, can result in the formation of a thick and hard crust that poses several problems in relation to maintenance, fuel consumption, and operational availability of ocean-going ships. Various ways of avoiding the fouling have been tried, but presently fouling is fought by the use of so-called antifouling paints, which slowly release biocides into the seawater.

In modern paints used for fouling control on commercial ships/vessels polishing is an essential feature ensuring that the biocide concentration at the surface is sufficient over time, and that the biofilm/macrofouling is minimized. In most paints the binder system polish slower than required for an effective diminishing of the fouling. The desired polishing rate is achieved by introduction of pigments and extenders/fillers in the paint. In commercial anti-fouling paints $Cu_2O$, Cuprous oxide, and/or ZnO, Zinc oxide is used to enhance polishing control. The restrictions on use of biocides in paints have placed the use of Cu and Zn under pressure, since Cu constitutes a permanent biocide load on the environment and Zn is bioaccumulating. It is therefore of interest to find suitable replacements for Cu and Zn compounds that might provide the same favorable polishing rates.

SUMMARY OF THE INVENTION

In order to overcome the above-mentioned limitations of the known compositions used for controlling the polishing process in paints used for fouling control, the present invention provides compositions comprising a gel wherein is entrapped at least one component. The loaded gel particles are referred to in the context of the present application as "S". "S" can enhance polishing in a controlled manner, either due to hydrolysis and/or due to suitable mechanical properties, and brings about a controlled leaching of the entrapped at least one component.

Generally a paint contains a binder, which is the film forming component of the paint, and particles of different kinds (pigments and/or fillers) in amounts up to the critical pigment volume concentration, also called CPVC, which is the limit for wetting all pigments/particles with the binder system. The polishing rate for paints can be considered the removal rate of the paint components.

Filling a paint with gel particles S will thus be possible up to the limit where the gel particles S—together with other particles included in a formulation—start to come into physical contact. The binder thus fills the voids in the loose packing of S particles. The ratio between binder and S is in this situation the critical concentration of S.

If the S particles polish faster, i.e. are removed faster from the surface of the paint than the binder, the disappearing S particles will create water channels in the surface of the paint and thereby allow attack on the paint to a certain depth below the surface, thus ensuring a sufficient polishing rate and thereby also a sufficient release rate, or leaching of the active compound(s)/biocide.

Another way to achieve a larger surface is to allow swelling of the particles at the surface.

To achieve a larger surface by creating water channels as discussed above, it may be beneficial if the S particles contain a water-soluble/water-degradable polymer or binder.

Applicants have now found that rosin, hydrogenated rosin or water-soluble/water-degradable polymerized derivatives thereof can be employed in this function.

Rosin is a natural non-volatile resinous mass obtained from *Pinus palustris* Miller and other species such as *Pinus linnae*. It is not a polymer, but primarily contains a mixture of discrete tricyclic diterpene carboxylic acids (abietic acid, pimaric acid and structural isomers of abietic acid, see FIG. 1), and small amounts of non-acidic components.

Rosin contains approximately 90% "rosin acids" (FIG. 1). The rosin acids are monocarboxylic acids and have a typical molecular formula $C_{20}H_{30}O_2$. The prominent rosin acids include abietic acid (and its isomeric forms) with conjugated double bonds, and pimaric acid with non-conjugated double bonds. The rosin acid molecules possess two chemically reactive centres, the double bonds and the carboxyl group.

Figure 2:
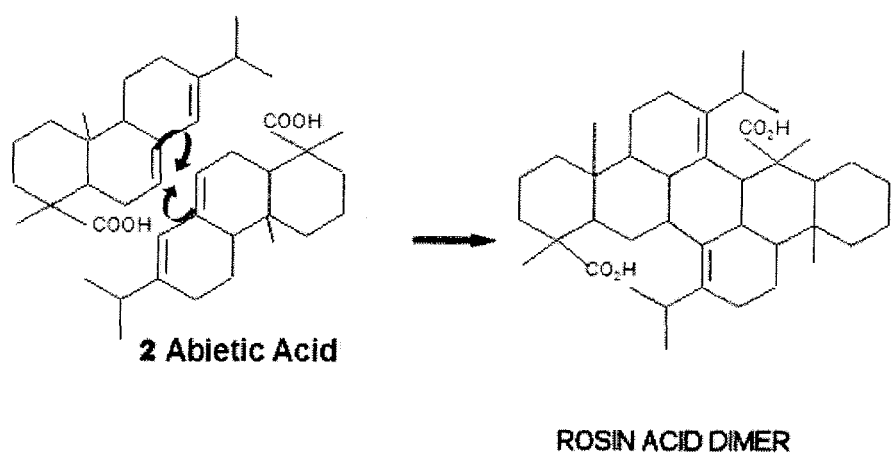

The double bonds of rosin acids can be polymerized to form eg. rosin dimer as shown in FIG. 2 for abietic acid.

The double bonds of of a rosin acid molecule can also be hydrogenated to form hydrogenated rosin—also known as tetrahydroabietic acid—which still contains a carboxylic group suited for ester formation, but no double bonds.

Figure 3:
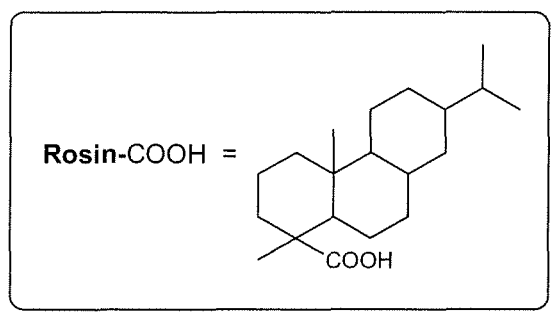
Figure 3:
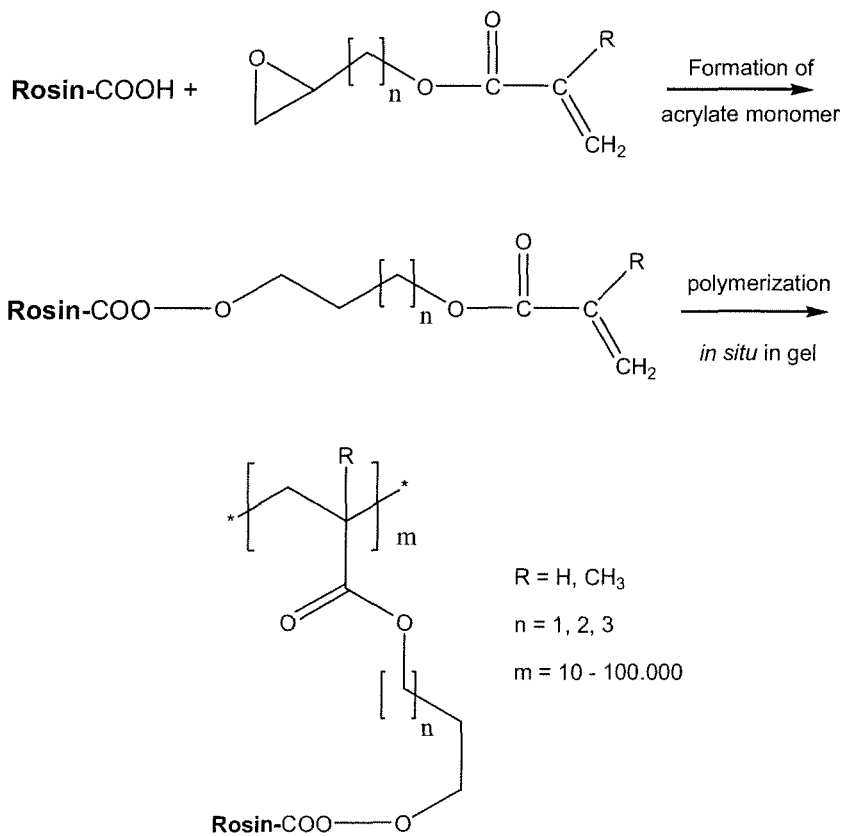

The carboxylic acid group of a rosin acid (including hydrogenated rosin) molecule can also be reacted with a linker to form a new polymerizable rosin derivative. In FIG. 3 it is shown how a linker of length 1-3 carbon atoms having an epoxy group in one end and an acrylate group in the other can react with the carboxyl group of the hydrogenated rosin acid to form a rosin derivative with a polymerizable acrylate group attached. The analogous derivative can be formed from rosin itself, ie. from abietic acid and its isomers.

This rosin derivative can be polymerized in situ in the gel thereby forming an acrylate backbone with grafted rosin moieties. The degree of polymerization is difficult ascertain within the gel, but the formed acrylate backbone presumably contains about 10.000-100.000 repeating rosin ester units.

The rosin immobilized in this manner will be immobilized in the gel in nonaquous media. However, when exposed to seawater at ph 8.2 the ester linkage will slowly hydrolyze and release Rosin. Loading of the gel can be realized with a rosin acrylate content up to 95 weight percent.

Due to its low solubility in water Rosin has been used in anti-fouling paints for many years as part of the binder system. Due to its good solubility in the solvents normally used in paints, rosin will end up as an integrated part of the binder phase in the paint film formation, and will thereby have a significant influence on the polishing rate of the paint film.

However, according to the present invention rosin may be introduced not only as part of the binder system, but also as part of the solid particles phase of the paint by filling or loading said gel particles S with rosin or a polymerized derivative thereof as discussed above. Rosin may be polymerized by several different means, for example by acid catalysis, heating, UV radiation or by free radical initiated polymerization.

When the loaded particles are exposed to sea water, not only the gel particles themselves can affect the polishing behavior, but also the rosin or water-soluble/water-degradable polymer inside the gel particles can take part in the polishing process.

Applicants have previously described the beneficial influence on the properties of paints when aerogels are added in PCT application WO 2009062975. These gels may entrap various mixtures of active compounds. In WO 2009062975 it was specified that the typical active component/active compound is so large that its release will primarily be determined by the breakdown of the gel network. The typical size of such compounds will be 1-2 nm.

The conditions according to the present invention are very different, as rosin is a natural substance of molecular weight approximately 300 Dalton and accordingly of much smaller dimensions than the entrapped components and compounds discussed in WO 2009062975.

Depending on the affinity towards different components in a paint formulation, rosin, rosin polymers or water-degradable polymers in general can leach out of a wet gel structure. In order to control the entrapment of such polymers, different methods can be used, which methods are the focus of the invention. By employing polymerized rosin or rosin derivatives, the pores of the final, dry gel particles S become "clogged" which prevents any minor amounts of non-polymerized material from escaping, until the gel structure itself has been polished sufficiently to expose a new layer of the gel particle.

In a first aspect the present invention thus relates to a method of producing polymer loaded gel particles for polishing control in anti-fouling paints by incorporation of one or more water-soluble or water-degradable polymers prepared from rosin or one or more rosin derivatives into a hosting gel structure, which method comprises the following steps:

a. Prepare a suitable dry gel and subsequently absorb said one or more water-soluble or water-degradable polymers in the gel by immersion of the gel particles in the relevant molten polymer or in a concentrated solution of said polymer, or b. Prepare a suitable dry gel and subsequently immerse the gel particles in a solution of the one or more relevant monomers necessary to produce said one or more water-soluble or water-degradable polymer, and subsequently carry out polymerization in situ, or c. Prepare a suitable wet gel (alcogel) and exchange the mother liquid in the wet gel with a saturated solution of said one or more water-soluble or water-degradable polymers, or d. Prepare a gel with a balanced hydrophobicity/hydrophilicity that will ensure that the gel—during the production of the paint—is partly filled with paint components such as for example said water-soluble or water-degradable polymers which have been dissolved in the binder phase of the paint, which steps are followed optionally by milling the polymer loaded gel particles obtained by any of the steps a-d above to finer particles, either before addition to a paint formulation, or during the further processing of the paint.

In an embodiment of the invention the hosting gel may be in wet form. In a different embodiment the hosting gel may be in a dried form such as as a xerogel, aerogel, cryogel or aeromosil.

The invention also allows for both the preparation of the hosting gel structure and the incorporation of the one or more water-soluble or water-degradable polymers to be conducted as a one pot synthesis in a high pressure vessel at sub- or supercritical conditions followed by venting solvents and byproducts from the reaction vessel at supercritical conditions or in gas phase before isolation of the loaded gel particles.

The present invention also relates to the polymer loaded gel particles obtained by the methods of the present invention discussed above, and to polymer loaded gel particles, wherein the method of preparation involves one or more steps conducted in the presence of carbon dioxide under supercritical conditions.

Loading rosin or one or more water-soluble/water-degradable polymers in gels by any of the above methods will have a significant effect on polishing properties and surface swelling of the eventual paint.

The gel may be an aerogel, a cryogel, a xerogel or an aeromosil depending on the requirement of the paint in question.

The polymer loaded particles may now be used as a combined pigment/binder component in the paint with a concentration that attains the desired polishing rate. Before mixing with the other paint components, the gel particles obtained by any of the above methods may be milled to finer particles either before addition to a paint formulation or during the further processing of the paint.

Since water-degradable polymers slowly hydrolyse in water, the gel particles will provide a means for penetration of water into the surface as discussed above. The gel structure may control the water penetration to an optimal surface area of the water degradable polymer, which allows control of the dissolution rate of said polymer.

The water-soluble/water-degradable polymers used may be mixed with suitable organic biocides on the list of accepted biocides, such as, for example, Econea™, Sea-Nine™ or soluble Pyrithiones. Hereby the release rate of the biocide is coupled to the dissolution of the water-soluble/water-degradable polymers and the distribution of gel particles in the paint. Furthermore the gel itself can be partly filled with acceptable biocides, thereby enhancing the biocidal effect.

The present invention thus also relates to the use of polymer loaded gel particles obtained by the methods of the invention as components for polishing control in anti-fouling paints.

In another aspect the present invention also relates to a method for achieving polishing control in anti-fouling paints, which method comprises adding polymer loaded gel particles obtained by the method of the invention to the relevant paint formulation during the processing of the paint.

In yet another aspect the present invention also relates to a method for improving the polishing rate of anti-fouling paints, which method comprises adding polymer loaded gel particles obtained by the method of the invention to the relevant paint formulation during the processing of the paint.

FIGURES

FIG. 1 shows the so-called "rosin acids", which are monocarboxylic acids and have a typical molecular formula $C_{20}H_{30}O_2$. The prominent ones include abietic acid with conjugated double bonds and pimaric acid with non-conjugated double bonds. Rosin acids are the main components of rosin.

FIG. 2 shows a polymerization reaction whereby two molecules of abietic acid are converted to a dimer.

FIG. 3 shows how a linker of length 1-3 carbon atoms having an epoxy group in one end and an acrylate group in the other can react with the carboxyl group of the hydrogenated rosin acid (tetrahydroabietic acid) to form a rosin derivative (monomer) with a polymerizable acrylate group attached. FIG. 3 further shows how this rosin derivative can be polymerized thereby forming an acrylate backbone with grafted rosin moieties. The degree of polymerization is difficult ascertain within the gel, but the formed acrylate backbone presumably contains about 10.000-100.000 repeating rosin ester units.

DEFINITIONS

The term "sol" as used herein means a solution of various reactants that are undergoing hydrolysis and condensation reactions. The molecular weight of the oxide species produced continuously increases. As these species grow, they may begin to link together in a three-dimensional network.

The term "alcogel" as used herein means a wet gel which can be removed from its original container and can stand on its own. An alcogel consists of two parts, a solid part and a liquid part. The solid part is formed by the three-dimensional network of linked oxide particles. The liquid part (the original solvent of the Sol) fills the free space surrounding the solid part. The liquid and solid parts of an alcogel occupy the same apparent volume.

The term "supercritical fluid" as used herein means a substance that is above its critical pressure and critical temperature. A supercritical fluid possesses some properties in common with liquids (density, thermal conductivity) and some in common with gases (fills its container, does not have surface tension).

The term "aerogel" as used herein means what remains when the liquid part of an alcogel is removed without damaging the solid part. Removal of the liquid part can be achieved by e.g. supercritical extraction. If made correctly, the aerogel retains the original shape of the alcogel and at least 50% (typically >85%) of the alcogel's volume.

The term "xerogel" as used herein means what remains when the liquid part of an alcogel is removed by evaporation, or similar methods. Xerogels may retain their original shape, but often crack. The shrinkage during drying is often extreme (~90%) for some xerogels.

The term "cryogel" as used herin means what remains when an alcogel is frozen and the previously liquid part of the alcogel is removed by evaporation keeping the alcogel frozen all the time. Cryogels may retain their original shape, but often crack. The shrinkage during drying may be substantial for some cryogels. Addition of suitable surfactants in the alcogel may relieve this problem.

The term "Aeromosil" as used herin means Organically Modified Silicate Aerogel, obtainable by modifying silicate aerogel structures with flexible, organic containing polymers such as polydimethylsiloxane (PDMS).

The empty gels of the invention in general have densities in the range 0.05 to 0.8 g/cm$^3$. When loading the gel the density will raise according to the amount and properties of the loaded compounds. Typically the densities of the loaded gels will be below 2.0 g/cm$^3$.

The absorption of rosin and other compounds in the aerogels renders the gels significantly denser than pure aerogels, but they are clearly distinguished from the dense glass films that may be prepared from the same starting gels by complete collapse as such films have densities similar to the corresponding glasses, i.e. 2.2 to 4.8 g/cm$^3$.

The term "rosin" as used herein comprises a material mainly consisting of abietic acid and its isomers, or hydrogenated Rosin which is a refined saturated (i.e. hydrogenated) reaction product. For the purpose of this invention, rosin may also be functionalized on the carboxylic group in order to obtain a polymerizable monomer, including esters and amides of abietic acid and its isomers.

The term "water degradable polymer" as used herein refers to polymers such as polyacrylates and -methacrylates containing chemical groups which upon contact with water may be hydrolyzed over time. Typical chemical groups comprise ester and amide groups.

The term "polishing rate" as used herein can be considered the removal rate of the paint components when a painted surface is exposed to seawater.

The ideal polishing rate for an anti-fouling paint is dictated by the type of vessel or pleasure boat the product is aimed for. Thus a low polishing rate is normally desired for ships sailing continuously, and a higher polishing rate for the yacht market. According to the present invention, polymer loaded gel particles can be produced which allow for a very wide range of polishing rates in the final anti-fouling paint, thus addressing the requirements of a broad segment of ships, yachts, boats, vessels, buoys, offshore structures and any other submerged objects and marine constructions, both stationary and non-stationary, for which fouling should be prevented.

DETAILED DESCRIPTION OF THE INVENTION

According to the present invention certain molecules such as rosin, hydrogenated rosin, water degradable rosin derivatives and/or water-degradable polymers thereof or other water-degradable polymers may be entrapped in gel particles, such as aerogel or aeromosil particles.

The resulting gel particles may be added to anti-fouling compositions such as paints to control the polishing rate of said compositions. Other components may be entrapped in the gel particles according to the invention, such as eg. biocides and/or metal particles which may have a beneficial influence on the properties of the eventual paints produced containing the gel particles.

In a preferred embodiment the gel particles of the invention are used in anti-fouling paints to provide polishing control.

In a first aspect the present invention thus relates to a method of producing polymer loaded gel particles for polishing control in anti-fouling paints by incorporation of one or more water-soluble or water-degradable polymers prepared from rosin or one or more rosin derivatives into a hosting gel structure, which method comprises the following steps:

a. Prepare a suitable dry gel and subsequently absorb said one or more water-soluble or water-degradable polymers in the gel by immersion of the gel particles in the relevant molten polymer or in a concentrated solution of said polymer, or b. Prepare a suitable dry gel and subsequently immerse the gel particles in a solution of the one or more relevant polymerizable monomers necessary to produce said water-soluble or water-degradable polymer, and subsequently carry out polymerization in situ, or c. Prepare a suitable wet gel (alcogel) and exchange the mother liquid in the wet gel with a saturated solution of said one or more water-soluble or water-degradable polymers, or d. Prepare a gel with a balanced hydrophobicity/hydrophilicity that will ensure that the gel—during the production of the paint—is partly filled with paint components such as for example said water-soluble or water-degradable polymers which have been dissolved in the binder phase of the paint.
followed optionally by milling the polymer loaded gel particles obtained by any of the steps a-d above to finer particles either before addition to a paint formulation or during the further processing of the paint.

In a specific embodiment of the invention the entrapment takes place by preparing a suitable dry gel and subsequently absorbing the relevant one or more water-soluble or water-degradable polymers in the gel by immersing the gel in molten polymer or a concentrated solution of said polymer.

In a preferred embodiment of the invention the one or more water-soluble or water-degradable polymers has a polyacrylate or polymethacrylate backbone.

In another specific embodiment of the invention the entrapment takes place by preparing a suitable dry gel followed by immersing said gel in a solution of the relevant one or more monomers necessary to produce said one or more water-soluble or water-degradable polymers, and subsequently carry out the polymerization of the adsorbed monomer in situ.

In another embodiment of the invention the entrapment takes place by exchanging the mother liquid in an already prepared wet gel (alcogel) with a saturated solution of the relevant one or more water-soluble or water-degradable polymers.

In a further embodiment of the invention the entrapment takes place by preparing a gel with a balanced hydrophobicity/hydrophilicity that will secure that the gel is partly filled with the relevant one or more water-soluble or water-degradable polymers during the production of the paint, said one or more water-soluble or water-degradable polymers having been dissolved in the binder phase of the paint.

In a specific embodiment the invention allows for both the preparation of the hosting gel structure and the incorporation of the one or more water-soluble or water-degradable polymers to be conducted as a one pot synthesis in a high pressure vessel at sub- or supercritical conditions followed by venting solvents and byproducts from the reaction vessel at supercritical conditions or in gas phase before isolation of the loaded gel particles.

In a preferred embodiment of the invention the one or more relevant monomers necessary to produce said water-soluble or water-degradable polymer are selected from rosin, rosin derivatives such as hydrogenated rosin, or abietic acid and isomers of abietic acid.

In a further preferred embodiment of the invention, the one or more relevant monomers necessary to produce said water-soluble or water-degradable polymer contain a polymerizable acrylate or methacrylate functionality or group.

In an embodiment of the invention one of the relevant monomers is rosin. In a different embodiment one of the relevant monomers is hydrogenated rosin. In a different embodiment one of the relevant monomers is hydrogenated rosin derivatized on the carboxy group to contain a linker with a polymerizable acrylate or methacrylate group attached. In a different embodiment one of the relevant monomers is selected from abietic acid and isomers of abietic acid.

In a further embodiment the relevant monomer is a rosin based product or derivative, which contains a hydrolyzable group such as an ester or amide.

In an embodiment of the invention the water-soluble or water-degradable polymers are created in situ from one or more relevant monomers by polymerization.

In another aspect the present invention also relates to the polymer loaded gel particles obtained by the methods of the present invention discussed above, and to polymer loaded gel particles, wherein the method of preparation involves one or more steps conducted in the presence of carbon dioxide under supercritical conditions.

In an embodiment of the invention the polymer loaded gel particles further comprise one or more biocides, such as, for example, Econea™, Sea-Nine™ or soluble Pyrithiones.

In another embodiment of the invention the polymer loaded gel particles further comprise metal particles, such as particles of Ag and/or Cu.

In another aspect the present invention also relates to the use of polymer loaded gel particles obtained by the methods of the invention as components for polishing control in anti-fouling paints.

In a specific embodiment the polymer loaded gel particles obtained by the methods of the invention are used as components for polishing control in anti-fouling paints for yachts and other types of private vessels.

In another specific embodiment the polymer loaded gel particles obtained by the methods of the invention are used as components for polishing control in anti-fouling paints for commercial ships and vessels.

In another specific embodiment the polymer loaded gel particles obtained by the methods of the invention are used as components for polishing control in anti-fouling paints for buoys, offshore structures and any other submerged objects.

In another specific embodiment the polymer loaded gel particles obtained by the methods of the invention are used as components for polishing control in anti-fouling paints for other types of both stationary and non-stationary marine constructions exposed to, or submerged in seawater.

In another specific embodiment the polymer loaded gel particles obtained by the methods of the invention are used as components for polishing control in anti-fouling paints for use in pipes and other parts of equipment including pumps and storage tanks designed for transporting or pumping non-potable water such as cooling water from power plants, waste water, sewage and the like.

In another aspect the present invention also relates to a method for achieving polishing control in anti-fouling paints, which method comprises adding polymer loaded gel particles obtained by the method of the invention to the relevant paint formulation during the processing of the paint.

In yet another aspect the present invention also relates to a method for improving the polishing rate of anti-fouling paints, which method comprises adding polymer loaded gel particles obtained by the method of the invention to the relevant paint formulation during the processing of the paint.

The present invention will in the following be exemplified by the following non-limiting examples:

EXAMPLE 1

Preparation of a Polymerizable Rosin Derivative 20.25 g hydrogenated rosin was dissolved in 100 ml dry Methyl ethyl ketone (MEK) and 72 mg hydroquinone and 360 mg tetramethylammoniumbromide were added. A solution of 11.6 g of glycidyl methacrylate is dissolved in 10 ml dry MEK and slowly added to the reaction mixture at room temperature. The reaction mixture is left under nitrogen atmosphere. After stirring for 15 min the temperature is raised to 80° C. and the reaction mixture is left for 24 hours.

After cooling the MEK is removed by destillation in vacuum. The waxy yellowish material is redissolved in methylene chloride and washed with a 5% aqueous solution of sodium hydroxide, followed by washing with a brine solution and finally with water. The methylene chloride solution is dried over sodium sulphate and the solvent is removed by vacuum desillation. The yield is 82%.

EXAMPLE 2

An aerogel prepared from TMOS as described:

86.5 ml TMOS (tetramethyl orthosilicate, tetramethoxysilane) was mixed with 400 ml MeOH on a magnetic stirrer for 15 minutes and 50 ml 0.5% ammonia solution added. After 2 minutes vigorous stirring the gel was allowed to rest unstirred and gelify within additionally 15 minutes.

300 g of the prepared gel was cut into pieces and placed in a 500 ml high pressure flow vessel. After slowly letting MeOH flow app ½ ml/minute for several days in order to remove water content, the temperature was raised to 40° C. and the vessel was gradually pressurized with MeOH to 100 bars with a speed of 3 bars/minute.

The reactor was flowed with $CO_2$ at 100 bars pressure and a temperature of 40° C. for 9 hours at a flow rate of 6-7 g $CO_2$/minut. After this, $CO_2$ gas was slowly vented off during several hours leaving the dry hydrophilic silica aerogel for collection from the vessel.

For preparation of more hydrophobic aerogels, MTMS (methyltrimethoxysilane) can partly be used as replacement for TMOS using the same procedure as described above.

EXAMPLE 3

The material produced in example 2 was crushed to produce small lumps below 1 $cm^3$ and immersed in a solution in dichloromethane of rosin-monomer and a few percent AIBN as polymerization initiator. After evaporation of solvent, xylene was added and the suspended material was heated to 85° C. Polymerisation was allowed to take place for about 15 minutes. The material was cooled down and washed several times with xylene in order to remove unreacted rosin-monomers and if necessary dried in vacuum before use.

EXAMPLE 4

An aerogel prepared from TMOS as described in example 2 was prepared. The material was crushed to produce small lumps below 1 $cm^3$ and placed in a container with a solution of Rosin and a Rosin based monomer in acetone. The container was heated to 60° C. where a solution of rosin can be obtained in acetone. The container was kept at a temperature between 60 and 80° C. for a time not exceeding 4 hours. The loaded gel was separated from the rosin and if necessary dried in vacuum before use.

EXAMPLE 5a

An aerogel prepared from TMOS as described in example 2 was prepared. The material was crushed to produce small lumps below 1 $cm^3$ and placed in a container with an excess of a mixture of Rosin based monomer and Econea™ (an organic biocide). The filled gel was separated from the molten rosin. The container with the filled gel was heated to 140° C. and kept at this temperature for a time not exceeding 4 hours.

EXAMPLE 5b

The Example 4a procedure was carried out with Sea-Nine™ as the biocide.

EXAMPLE 6a

An aerogel prepared from TMOS as described in example 2 was prepared. The material was crushed to produce small lumps below 1 $cm^3$ and placed in a container with a solution of Rosin based monomer and Econea™ (an organic biocide) in acetone. The container was heated to about 52° C. where a solution of rosin and Econea™ in acetone was obtained. The container was kept at this temperature for about 4 hours. The filled gel was separated from the solution of the rosin and dried in vacuum before use.

EXAMPLE 6b

The Example 5a procedure was carried out with Sea-Nine™ as the biocide.

EXAMPLE 7

As example 5a, but the container was pressurized with carbon dioxide at sub or supercritical conditions as the solvent. The solvent and possible co-solvents were vented out as a gas, preferably after cooling of the vessel.

EXAMPLE 8

An aeromosil was prepared according to the detailed description in ref.1[1], but instead of the Pd-diiminate, Rosin based monomer and biocides were added. All reaction components were mixed together in the amounts described in Table 1, directly in a 10 ml high pressure reaction vessel with a stirring magnet. The reactor was heated to 40° C. and $CO_2$ applied to a pressure of about 500 bars.

[1] Jespersen H. T. et al, J. of Supercritical Fluids 46 (2008) 178-184

The reaction was allowed to continue for 48 h totally. The unreacted components and by-products were removed by slowly releasing the pressure during several hours, and a slightly acidic AEROMOSIL hosted Rosin containing matrix could be collected from the reactor.

TABLE 1

| | |
|---|---|
| TMOS | 1.79 g |
| Formic acid | 2.14 g |
| PDMS-S14 | 0.71 g |
| Rosin | 0-5 g |
| Biocides | 0-5 g |

The invention claimed is:

1. A method of producing polymer loaded gel particles for polishing control in anti-fouling paints by incorporation of one or more water-soluble or water-degradable polymers prepared from rosin or one or more rosin derivatives into a hosting gel structure, which method comprises the following steps:
   a) Prepare a suitable dry gel and subsequently immerse the gel particles in a solution of the one or more relevant monomers necessary to produce said water-soluble or water-degradable polymer prepared from rosin or one or more rosin derivatives, and subsequently carry out polymerization of said water-soluble or water-degradable polymer in situ, or
   b) Prepare a suitable wet gel (alcogel) and exchange the mother liquid in the wet gel with a saturated solution of said one or more water-soluble or water-degradable polymers prepared from rosin or one or more rosin derivatives;
   wherein, the method further comprising the step of milling the polymer loaded gel particles obtained by any of the steps a)-b) to finer particles either before addition to a paint formulation or during the further processing of the paint.

2. The method of claim 1 wherein the hosting gel is a dry xerogel, aerogel, cryogel or aeromosil.

3. The method of claim 1, wherein the one or more water-soluble or water-degradable polymers are created in situ from a relevant monomer by polymerization.

4. The method of claim 1, wherein the one or more relevant monomers necessary to produce said water-soluble or water-degradeable polymers are selected from the group consisting of rosin, rosin derivatives, abietic acid, and isomers of abietic acid.

5. The method of claim 1, wherein the polymer loaded gel particles further comprise one or more biocides.

6. The method of claim 4 wherein the biocide is a soluble pyrithione.

7. The method of claim 1, wherein the polymer loaded gel particles further comprise metal particles.

8. The method of claim 7 wherein the metal particles are selected from the group consisting of particles of Ag, Cu, and a mixture thereof.

9. Polymer loaded gel particles obtained by the method of claim 1.

10. Polymer loaded gel particles according to claim 9 wherein the method of preparation involves one or more steps conducted in the presence of carbon dioxide under supercritical conditions.

11. A method for achieving polishing control in anti-fouling paints, which method comprises adding polymer loaded gel particles obtained by the method of claim 1 to the relevant paint formulation during the processing of the paint.

12. A method for improving the polishing rate of anti-fouling paints, which method comprises adding polymer loaded gel particles obtained by the method of claim 1 to the relevant paint formulation during the processing of the paint.

13. The method of claim 1, wherein the polymer loaded gel particles are produced by step a).

14. The method of claim 1, wherein the wherein the polymer loaded gel particles are produced by step b).

* * * * *